US010773032B2

(12) United States Patent
Cirillo et al.

(10) Patent No.: US 10,773,032 B2
(45) Date of Patent: Sep. 15, 2020

(54) MONITORING DEVICE

(71) Applicant: CAREBAY EUROPE LTD, Sliema (MT)

(72) Inventors: William Robert Cirillo, Dublin (IE); John Pascal Hughes, Dublin (IE)

(73) Assignee: SHL MEDICAL AG, Zug (CH)

( * ) Notice: Subject to any disclaimer, the term of this patent is extended or adjusted under 35 U.S.C. 154(b) by 145 days.

(21) Appl. No.: 15/125,996

(22) PCT Filed: Mar. 13, 2015

(86) PCT No.: PCT/IE2015/000002
§ 371 (c)(1),
(2) Date: Sep. 14, 2016

(87) PCT Pub. No.: WO2015/136513
PCT Pub. Date: Sep. 17, 2015

(65) Prior Publication Data
US 2017/0189625 A1 Jul. 6, 2017

(30) Foreign Application Priority Data
Mar. 14, 2014 (IE) .................................. S2014/0072

(51) Int. Cl.
*A61M 5/50* (2006.01)
*A61M 5/315* (2006.01)
(Continued)

(52) U.S. Cl.
CPC ............ *A61M 5/5086* (2013.01); *A61M 5/20* (2013.01); *A61M 5/24* (2013.01); *A61M 5/3155* (2013.01);
(Continued)

(58) Field of Classification Search
CPC .......... A61M 5/31568; A61M 5/31525; A61M 2005/3126; A61M 2205/3313;
(Continued)

(56) References Cited

U.S. PATENT DOCUMENTS 5,792,117 A * 8/1998 Brown ............... A61B 5/14532
604/207
5,814,015 A * 9/1998 Gargano ............. A61M 5/1456
604/151

(Continued)

FOREIGN PATENT DOCUMENTS

WO  2009/024562   2/2009
WO  2010/128493   11/2010
(Continued)

OTHER PUBLICATIONS

International Search Report and Written Opinion for Int. App. No. PCT/IE2015/000002, dated Jul. 3, 2015.
(Continued)

*Primary Examiner* — Laura A Bouchelle
*Assistant Examiner* — Justin L Zamory
(74) *Attorney, Agent, or Firm* — McDonnell Boehnen Hulbert & Berghoff LLP

(57) ABSTRACT

A smart monitoring device for automatically monitoring the injection of medicines such as insulin which can be retrofitted to a conventional insulin pen in which the device has an optical motion sensor for detecting actuation of the injection pen together with an optional accelerometer sensor, medicament temperature and mounting sensors, the monitoring device being communicable with external smart devices such as smartphones.

19 Claims, 16 Drawing Sheets

(51) Int. Cl.
*G01D 5/34* (2006.01)
*A61M 5/24* (2006.01)
*A61M 5/20* (2006.01)
*A61M 5/31* (2006.01)

(52) U.S. Cl.
CPC ........... *A61M 5/31525* (2013.01); *G01D 5/34* (2013.01); *A61M 2005/3126* (2013.01); *A61M 2205/3313* (2013.01); *A61M 2205/3331* (2013.01); *A61M 2205/3368* (2013.01); *A61M 2205/3569* (2013.01); *A61M 2205/3584* (2013.01); *A61M 2205/502* (2013.01); *A61M 2205/587* (2013.01); *A61M 2205/60* (2013.01); *A61M 2209/08* (2013.01); *A61M 2230/63* (2013.01)

(58) Field of Classification Search
CPC .... A61M 2205/3368; A61M 2205/502; A61M 2205/587; A61M 2205/60
See application file for complete search history.

(56) References Cited

U.S. PATENT DOCUMENTS 6,482,185 B1 * 11/2002 Hartmann ......... A61M 5/31525
604/189
2004/0024364 A1 * 2/2004 Langley ............ A61M 5/14244
604/187
2008/0312604 A1 * 12/2008 Boesen ................. A61M 5/008
604/207
2010/0286612 A1 * 11/2010 Cirillo ............... A61M 5/31525
604/111
2011/0264033 A1 * 10/2011 Jensen ................ A61M 5/1452
604/65
2015/0018775 A1 * 1/2015 Groeschke .............. A61M 5/24
604/207

FOREIGN PATENT DOCUMENTS

| WO | 2011/117212 A1 | 9/2011 |
| WO | 2013/004843 A1 | 1/2013 |
| WO | 2013/004844 | 1/2013 |
| WO | 2013/120775 A1 | 8/2013 |
| WO | 2013/120778 | 8/2013 |
| WO | 2014023763 | 2/2014 |

OTHER PUBLICATIONS

European Office Action for EP Application No. 15719006.7, dated Jun. 25, 2020.

* cited by examiner

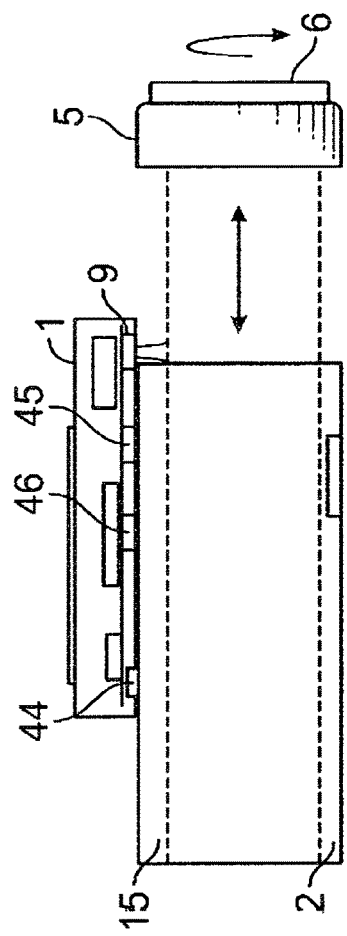
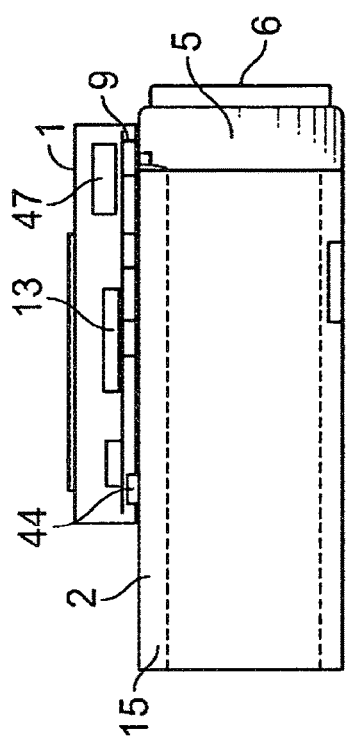
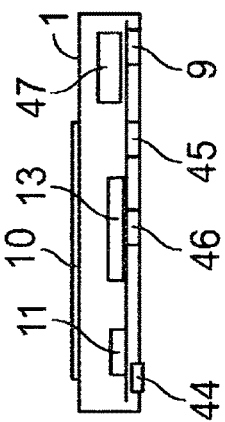
FIG. 15
FIG. 16
FIG. 17

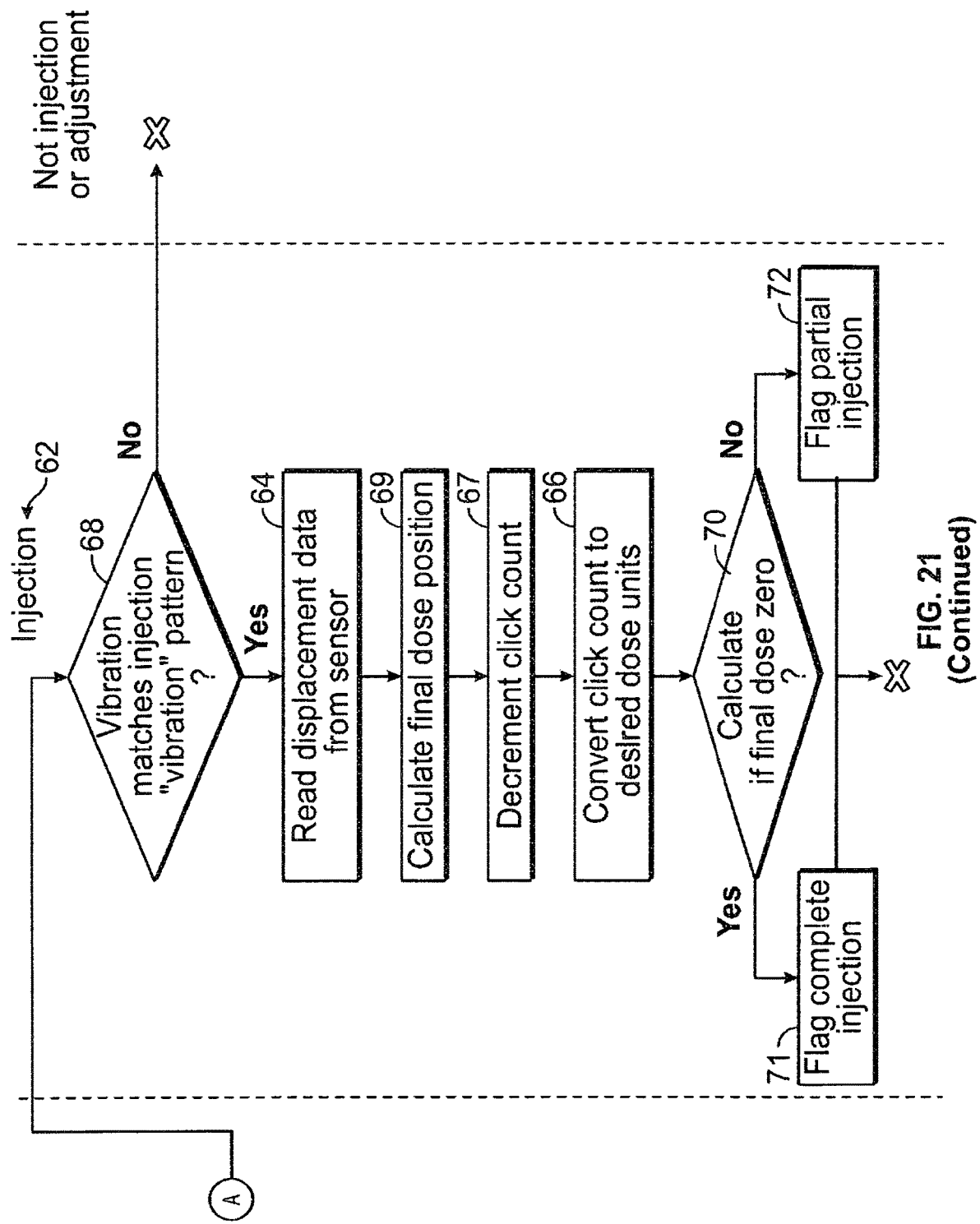

MONITORING DEVICE

CROSS REFERENCE TO RELATED APPLICATIONS

The present application is a U.S. National Phase Application pursuant to 35 U.S.C. § 371 of International Application No. PCT/IE2015/000002 filed Mar. 13, 2015, which claims priority to Irish Patent Application No. S2014/0072 filed Mar. 14, 2014. The entire disclosure contents of these applications are herewith incorporated by reference into the present application.

TECHNICAL FIELD

This invention relates to a monitoring device and more particularly to a device for monitoring and managing the injection of medicines such as insulin and to an injection device incorporating such a monitoring device.

BACKGROUND

Individuals diagnosed with some chronic illnesses are often prescribed medicines that must be injected at regular intervals. In general, it is necessary for patients to inject themselves with the medication. One of the most common self-injected medications is insulin which is prescribed in the treatment of diabetes.

In the following description, for the sake of convenience, the monitoring device of the invention and injection devices incorporating the monitoring device will be described in relation to diabetes patients and insulin injection pens used by those patients. However, as will be appreciated by those skilled in the art, the problems faced by insulin users are increasingly common to many medical conditions, such that the monitoring devices and injection devices (such as pens of the invention incorporating the monitoring devices) have wide application in the dosing of a wide range of medications for various medical conditions. Accordingly, the invention should not be construed as being limited to the automatic monitoring of insulin dosages or the treatment of diabetes.

Those diagnosed with diabetes know that much of their long-term health depends on good diabetes management. Tracking one's diabetes and managing glucose and insulin levels is essential in order to avoid serious complications such as increased morbidity and mortality, cardiovascular, cerebrovascular and peripheral vascular disease.

Type 1 diabetes is diagnosed when the body fails to produce sufficient insulin with the result that a periodic insulin injection is required to control glucose levels in the body. A major risk with insulin injection is accidental or inadvertent insulin overdose. An insulin overdose results in very low blood sugar levels (hypoglycemia) giving rise to symptoms such as headache, irregular heartbeat, increased heart rate or pulse, sweating, tremor, nausea, increased hunger, disorientation and anxiety. Failure to rapidly diagnose and treat hypoglycemia can lead to coma.

Diabetes patients generally employ injection devices known as insulin pens and it is imperative for insulin pen users to keep accurate track of the type and amount of insulin they are injecting.

Individual insulin products are numerous, but insulin may be divided into four major types. Short-acting insulin is a soluble insulin that acts quickly (30-60 minutes) and lasts for between 6 and 8 hours while some types may be faster-acting and shorter-lasting. Intermediate-acting insulin or Isophane insulin acts at a slightly slower rate (1-2 hours) and lasts for between 10 and 14 hours while long-acting insulin (e.g. insulin detemir, insulin glargine, protamine zinc insulin and insulin zinc suspension) act slowly (1-2 hours) and last for up to 24 hours. Mixtures of insulin such as mixed short and intermediate-acting insulin in accordance with an individual's needs can also be used.

As indicated above, insulin pen users can suffer long-term health consequences if they do not adhere accurately and carefully to a dosage schedule.

However, insulin pens and similar devices are nor smart devices. No method exists for automatically monitoring the intake of insulin using insulin pens—typically manual paper records must be maintained by the user or smart handheld devices such as mobile phones or tablets can be used to again manually store insulin dosages and patterns.

More particularly, it is not currently possible to accurately and effectively automatically record and monitor insulin injections administered via insulin pens. Moreover, manual recording by end users whether on paper or smart handheld devices does not allow for individual patient insulin dosages to be recommended (to the patient) and reported (to a medical professional) for analysis. In short, known insulin pens frequently fail to protect users from under or over dosages.

Attempts have been made to develop monitoring devices for injection devices that record dosages and transmit the dosage data to remote devices. For example, it is known to use monitoring devices fitted with cameras and Optical Character Recognition (OCR) units to simply photograph and record the dosage displayed on the dosage display of the injection pens. However, such monitoring devices can be difficult to position over the dosage display for the camera to photograph the dosage, while even if correctly positioned the display can be difficult for the camera to read depending on its format. This is particularly the case where non-Roman numerals are displayed. Moreover, OCR requires such a high processing power that it may not be possible to process the data on a small monitoring device and external processing power may be required giving rise to additional complexity and manufacturing cost. In addition, the camera used must provide extremely high levels of clarity for the OCR software giving rise to significant camera hardware costs that can be prohibitive while the associated optics are also complex and necessarily expensive.

SUMMARY

According to the invention there is provided a device for monitoring the injection of a medicine via an injection device comprising:

an optical motion detection system for detecting actuation of the injection device.

Preferably, the optical motion detection system comprises an optical sensor.

More preferably, the optical sensor is selected from the group comprising a visible light, infra red, laser LED, ultra violet, visible LED optical sensor.

Most preferably, the optical sensor comprises a visible light or laser LED optical sensor.

Preferably, the optical motion detection system further comprises a memory, a CPU and a display communicable with the optical sensor.

More preferably, the optical motion detection system comprises a communications module for communicating between the monitoring device and an external smart device.

Most preferably, the communications module comprises a Bluetooth communications module.

Suitably, the external smart device comprises a smartphone or similar computer or handheld device.

Preferably, the device further comprises an accelerometer sensor for detecting vibration of the injection device.

Advantageously, the device further comprises a temperature sensor for monitoring the temperature of the medicine.

Optionally, the monitoring device comprises an attachment means for retrofitting the monitoring device to an injection device to create a smart injection device.

Preferably, the attachment means comprises a detachable attachment means and, more preferably, the detachable attachment means comprises a sleeve mountable on the injection device.

Suitably, the sleeve is unique to the injection device.

In a preferred embodiment, the sleeve comprises at least one injection device identifier for communicating the identity of the injection device to the monitoring device. Preferably, the injection device identifier comprises a projection on the sleeve.

Advantageously, the monitoring device comprises an injection device identifier sensor. Preferably, the injection device identifier sensor comprises a pressure sensor.

In a preferred embodiment of the invention, the injection device comprises an injection pen.

The invention also extends to an injection pen comprising a device as hereinbefore defined.

Preferably, the injection pen is an insulin injection pen.

In short, in one embodiment, the invention therefore provides a clip-on device that attaches to injection devices such as insulin pens to assist in maintaining optimum control of a medical condition by recording, monitoring, recommending, reporting, and protecting a user.

The monitoring device can be in the form of a clip-on insulin recorder that is retrofitted to a standard known insulin pen to automatically assist in maintaining optimum diabetic control i.e. to assist users in conforming to a prescribed injection schedule, in adhering to prescribed dosage, in avoiding extra injections, in avoiding missed injections and in adhering to recommended health and safety best practices in needle usage.

The devices of the invention are also adapted to ensure that the insulin is kept within the recommended temperature range.

The monitoring device and injection devices such as insulin pens incorporating the device of the invention are both small enough to be easily carried by users wherever they go. The monitoring device can be retro-fitted as an attachment to existing standard insulin pens or incorporated into injection pens during manufacture.

Because it is the case that the better the records that user's keep, the better their condition can be monitored and analysed, the monitoring device and insulin pen of the invention result in better and healthier lifestyles with reduced or negligible risks of insulin over or underdoses.

The devices of the invention assist in effective diabetes management and provide a quick and easy method of automatically recording insulin injection dosage records whilst also issuing reminders or other user warnings to assist in the management of the condition.

The devices of the invention are adapted to automatically record and generate usage records which enable report generation and help to identify trends and patterns in users' insulin intake so adjustments can be made in medication, exercise, or eating regimes to in turn provide users and their medical professionals with a long-term view of their disease to help control the disease and lead a healthier life without complications.

The benefits of the invention can be summarized as follows. The monitoring device can be in the form of a clip-on insulin recorder that can be retro-fitted to known existing insulin pens to assist in maintaining optimum diabetic control i.e. assist in conforming to a prescribed injection schedule, in adhering to prescribed dosage, in avoiding extra injections and in avoiding missed injections. The retro-fittable monitoring device can be easily coupled with a conventional insulin pen and may be removed from one pen and coupled with another pen as required. The devices of the invention can record and transmit data so that dosages of insulin may be electronically recorded for an individual user. Finally, the monitoring devices of the invention and pens incorporating or retro-fitted with the monitoring devices do not require a user to manually or otherwise record data (such as measurements) taken from the pen.

BRIEF DESCRIPTION OF THE DRAWINGS

The invention will now be described, by way of example only, with reference to the accompanying drawings in which:

FIG. 15 is a schematic side elevation of the monitoring device mounted on an injection pen with the plunger shaft in the charged position ready for injection and with the rotational and longitudinal direction of movement of the dose selector and plunger shaft indicated by the arrows;

FIG. 16 is a schematic side elevation of the monitoring device with the plunger shaft in the injected position;

FIG. 17 is a schematic drawing of the monitoring device indicating the position of the optical motion sensor, the temperature sensor, the accelerometer sensor and the mounting sensor on the monitoring device;

DETAILED DESCRIPTION

Figure 1:
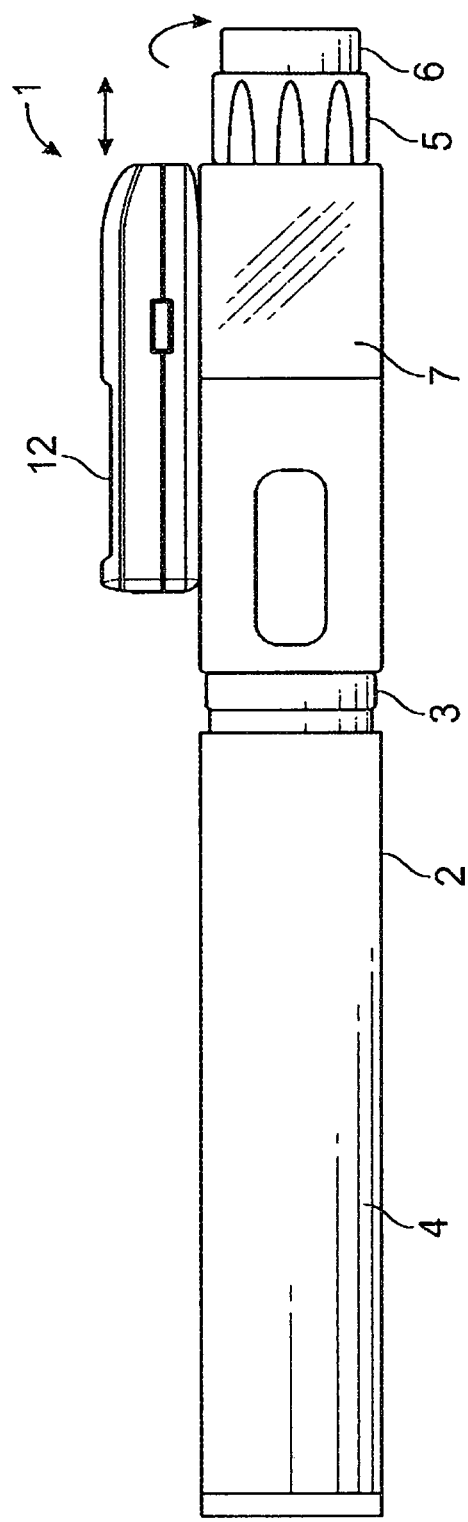
FIG. 1 is a side elevation of a conventional insulin pen retrofitted with a smart monitoring device in accordance with the invention with the rotational and longitudinal direction of movement of the dose selector and plunger shaft indicated by the arrows.
Figure 2:
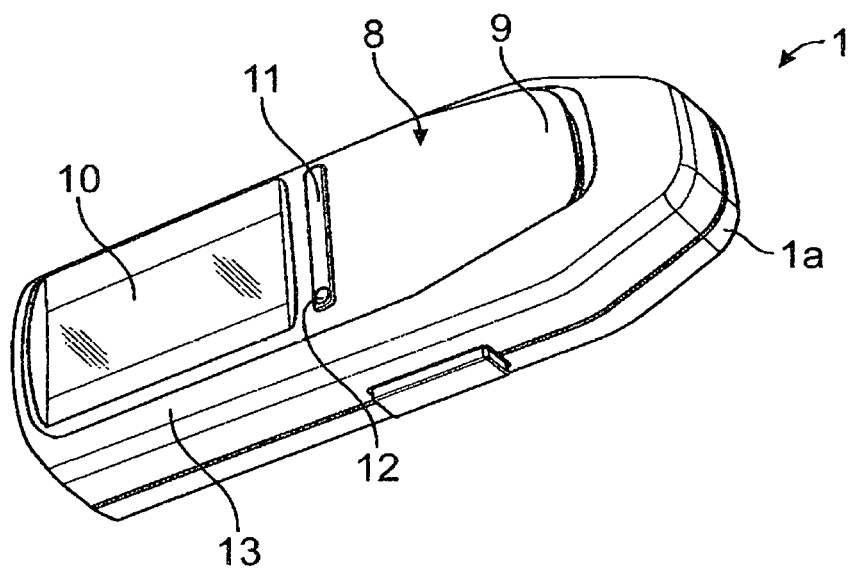
FIG. 2 is an enlarged perspective view from above and one side of the monitoring device of FIG. 1 detached from the insulin pen.
Figure 3:
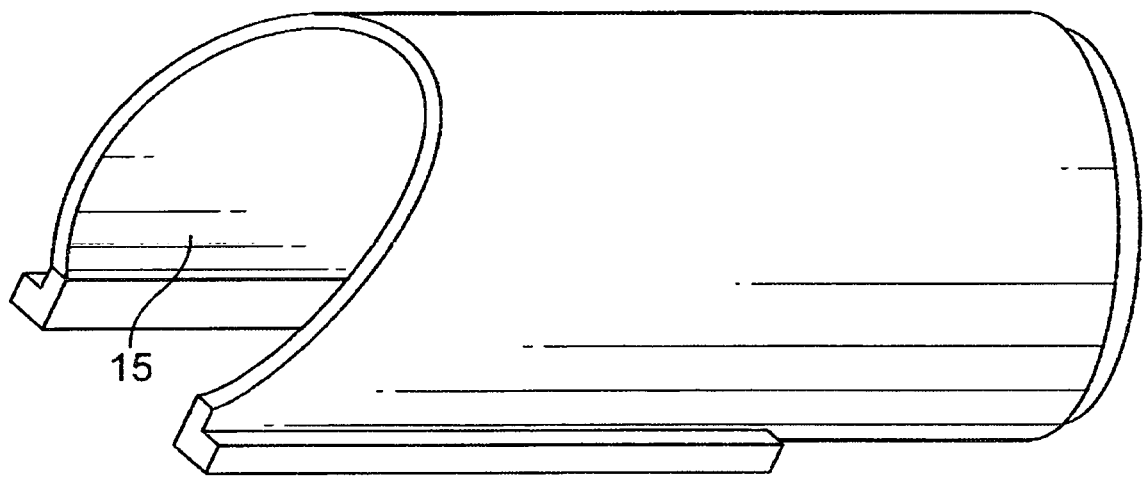
FIG. 3 is an enlarged perspective view from above and one side of the mounting clip or sleeve for retrofitting the monitoring device to the insulin pen.
Figure 4:
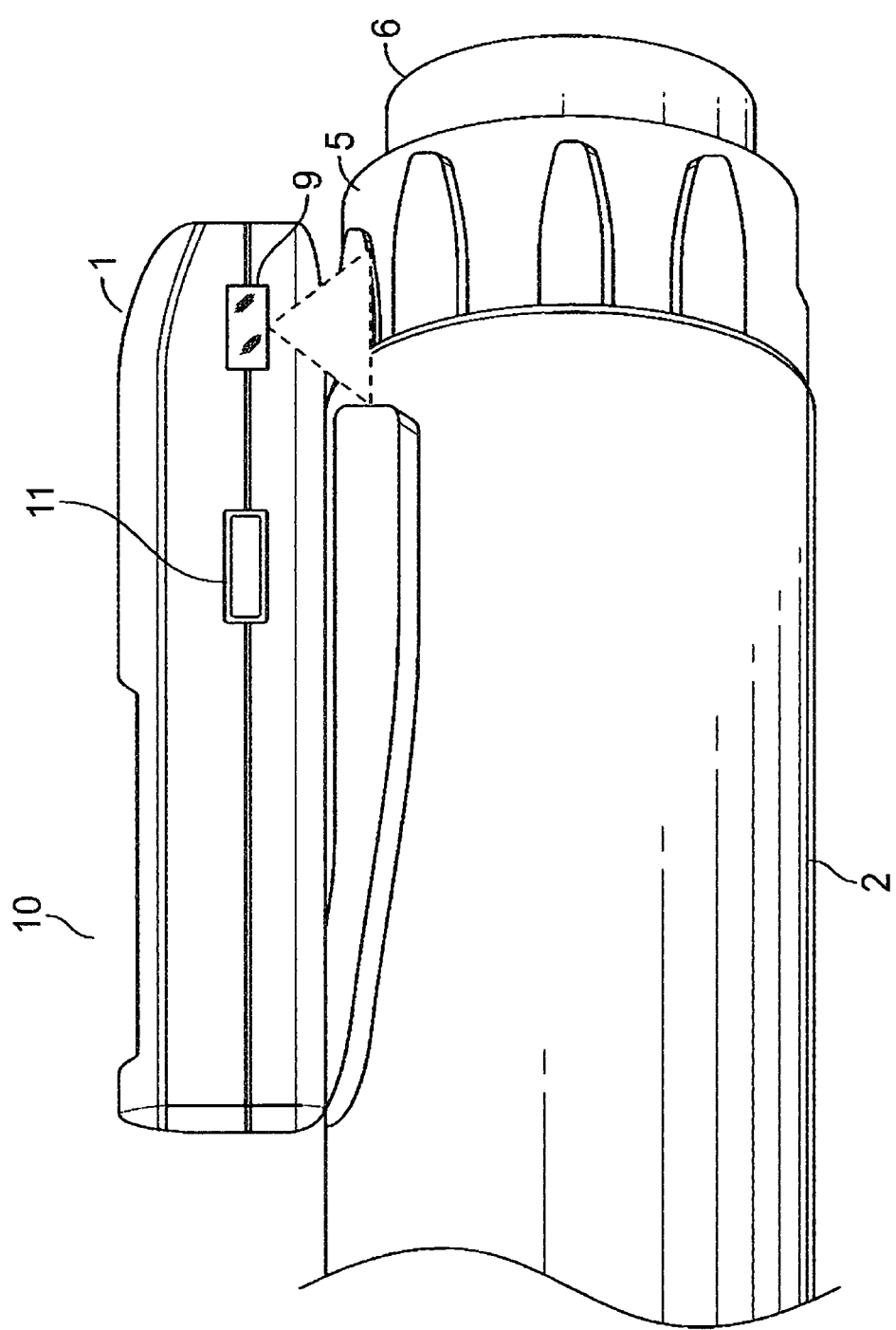
FIG. 4 is an enlarged side perspective view of the monitoring device of FIG. 1 on the insulin pen at the dose selector of the pen.
Figure 5:
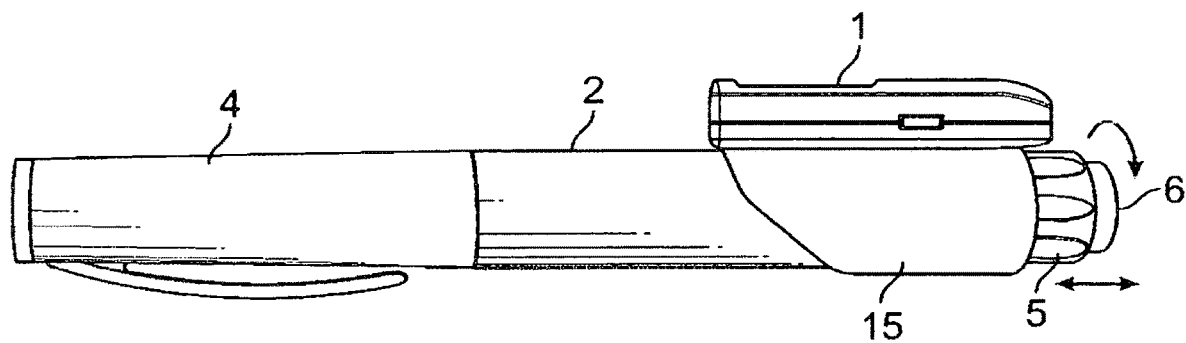
FIG. 5 is an enlarged side elevation of the smart monitoring device on the insulin pen with the rotational and longitudinal direction of movement of the dose selector and plunger shaft indicated by the arrows.

As shown in FIGS. 1 to 7, a first embodiment of a smart monitoring device for automatically monitoring the injection of medicines such as insulin is generally indicated by the reference numeral 1. In the present embodiment, the monitoring device 1 is retrofitted to a standard, conventional and commercially available insulin pen 2 of the type well-known in the art. However, as will be appreciated by those skilled in the art, the monitoring device can be integrated into insulin pens during manufacture if desired.

The conventional insulin pen 2 is generally made up of a pen body 2 housing a needle and plunger for depressing the needle at one end of the insulin pen 2 (not shown), a cap 4 for protecting the needle and a rotatable dose selector 5 at the other end of the insulin pen 2. The rotatable dose selector 5 surrounds a push button 6 which projects from the insulin pen 2 in the conventional manner. The dose selector 5 and the push button 6 together define a shaft which is rotatable and longitudinally moveable in the directions indicated by the arrows in FIGS. 1 and 5. The push button 6 effects depression of the plunger to eject insulin from the insulin pen 2 into a patient via the needle in use.

A mechanical dose display 7 is disposed adjacent the rotatable dose selector 5 to show the selected dose.

Figure 6:
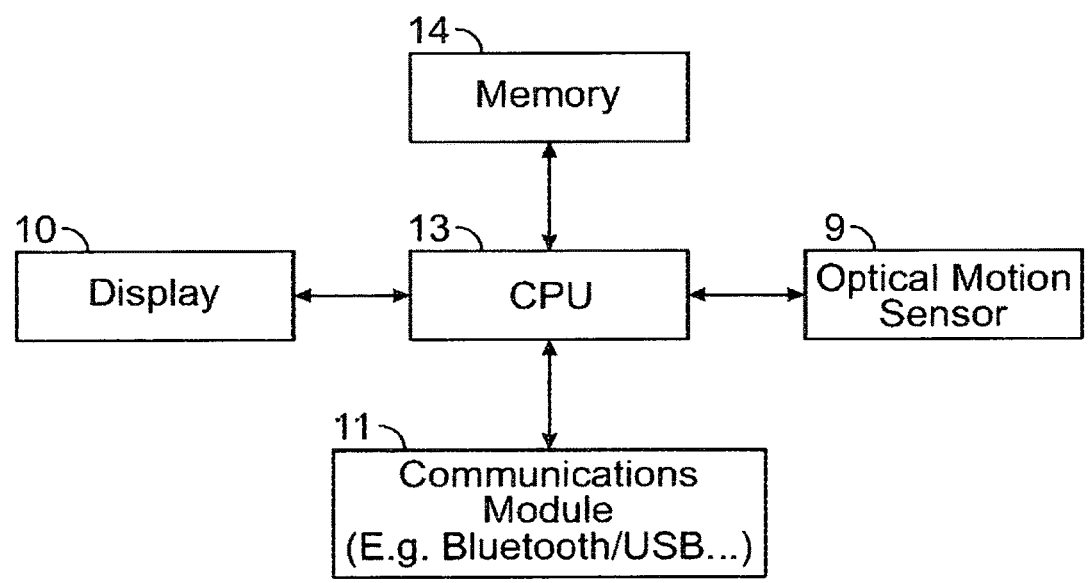
FIG. 6 is a functional block diagram of the motion detection system of the monitoring device.
Figure 7:
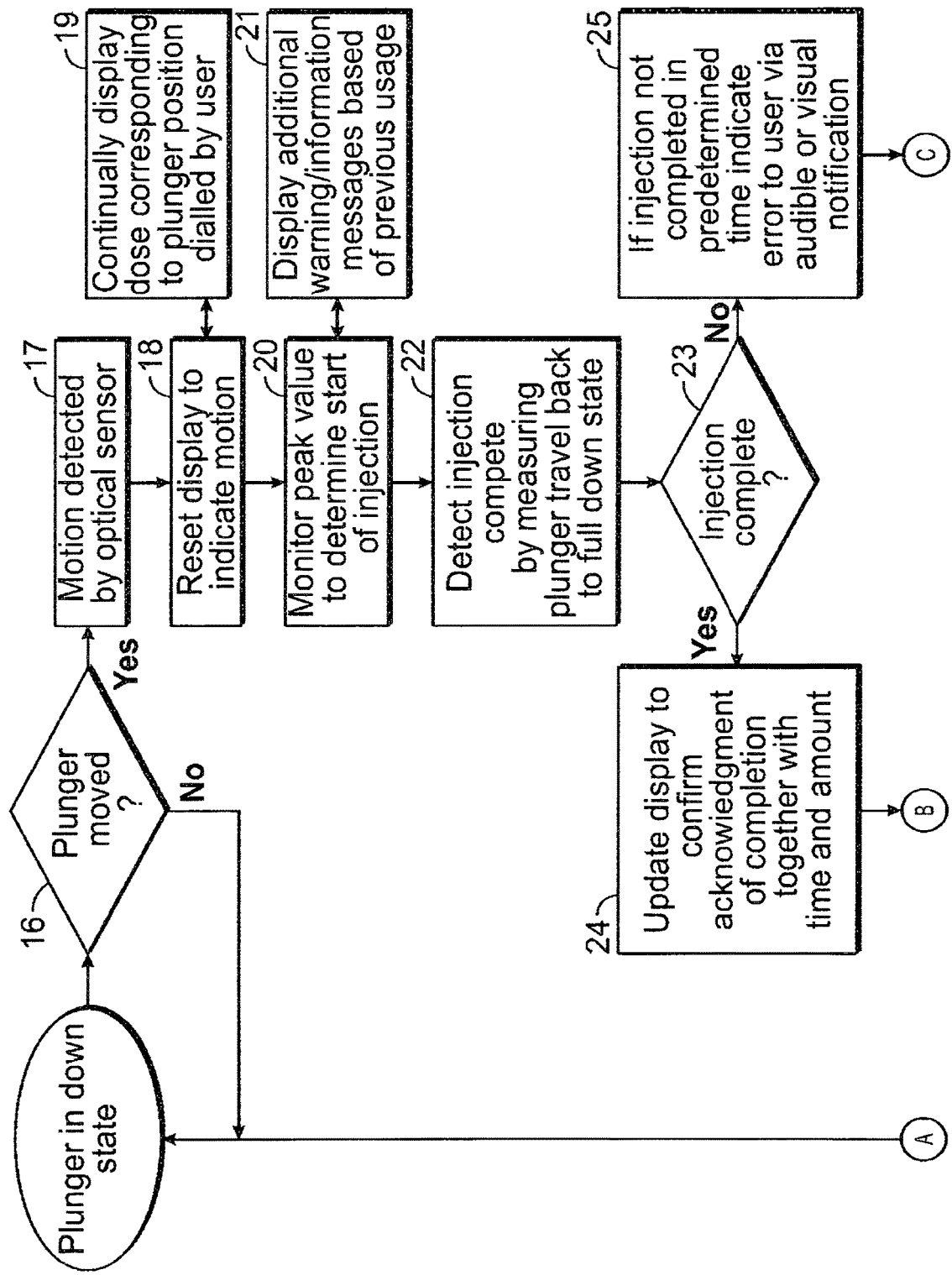
FIG. 7 is a flow diagram of the operation of the monitoring device of the first embodiment of the invention.
Figure 7:
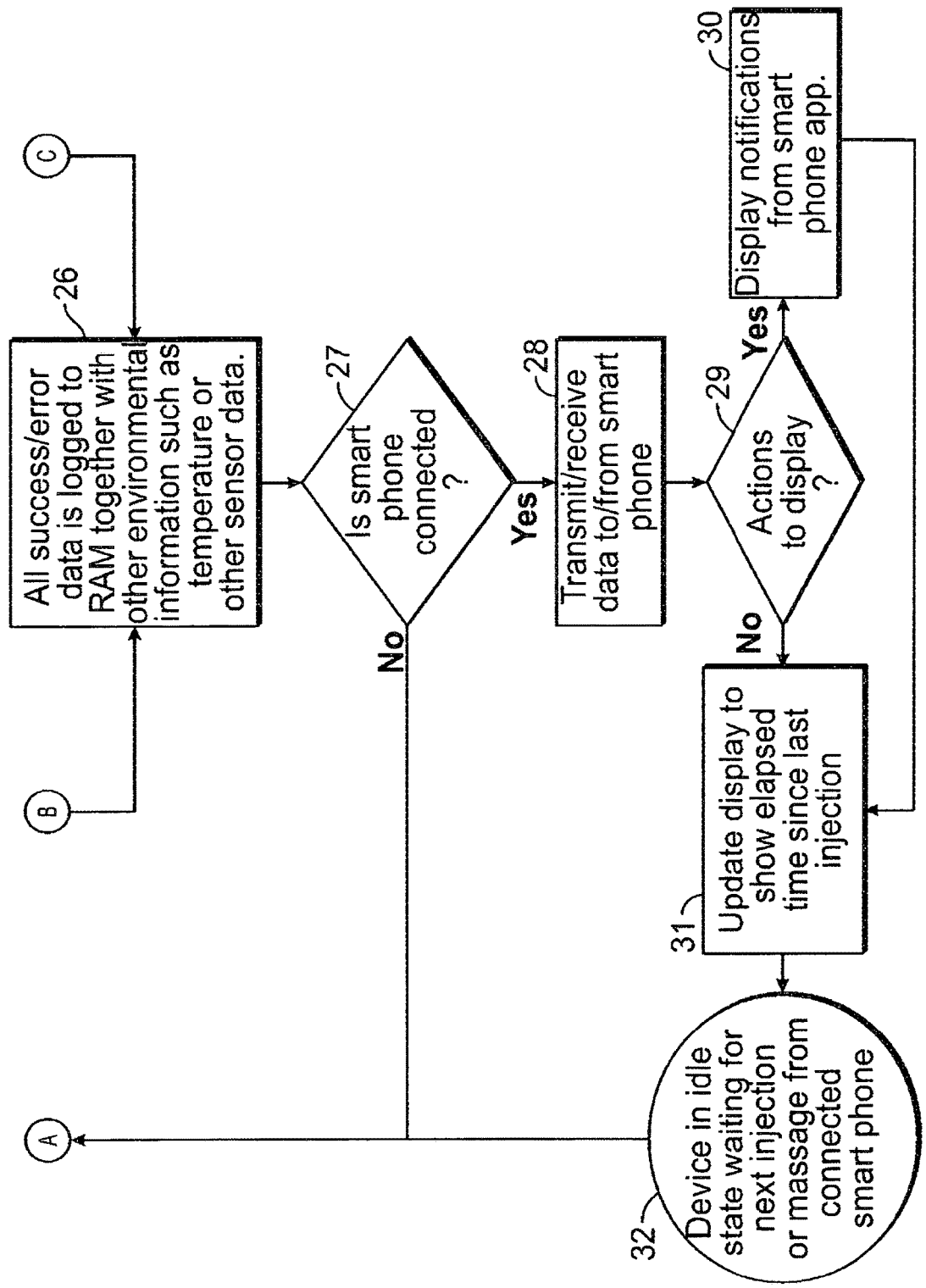
Figure 8:
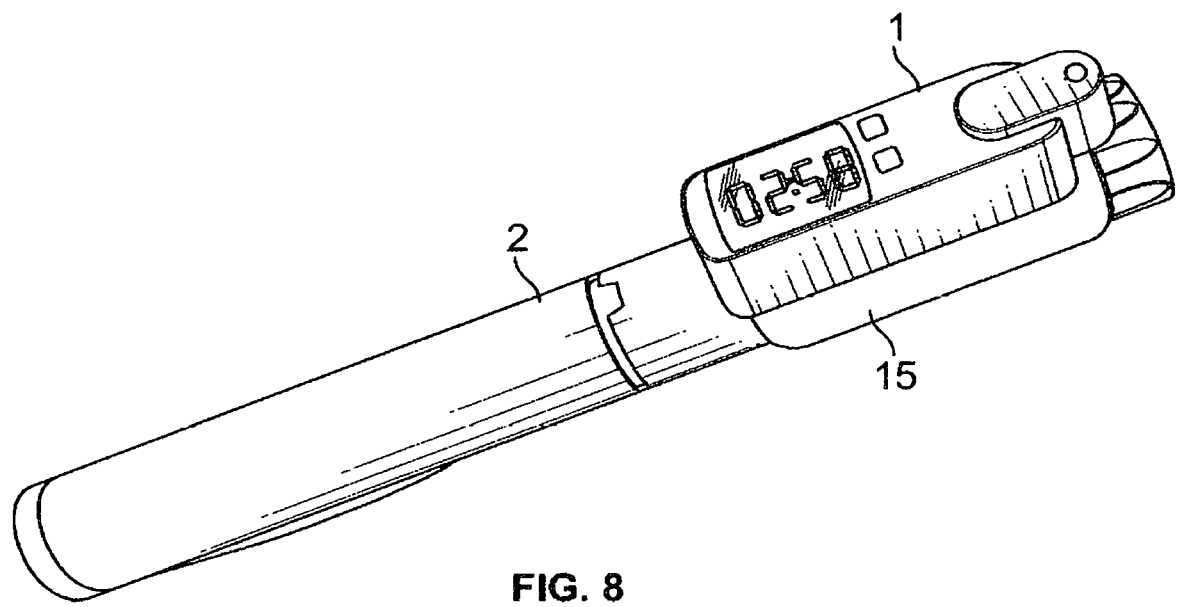
FIG. 8 is a perspective view from above and one side of a second embodiment of a monitoring device of the invention having a mounting sensor, an accelerometer sensor and a temperature sensor, mounted on an injection pen via a sleeve adapted to fit the specific injection pen and communicate the identity of the injection pen to the monitoring device.
Figure 9:
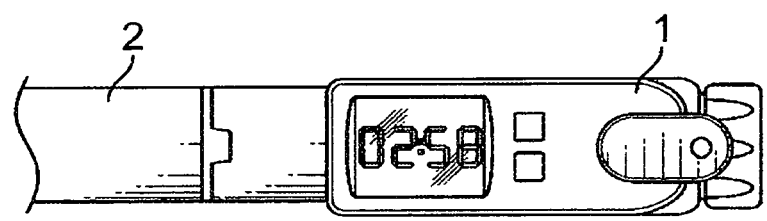
FIG. 9 is a top plan view of the monitoring device of FIG. 8 on the injection pen.
Figure 10:
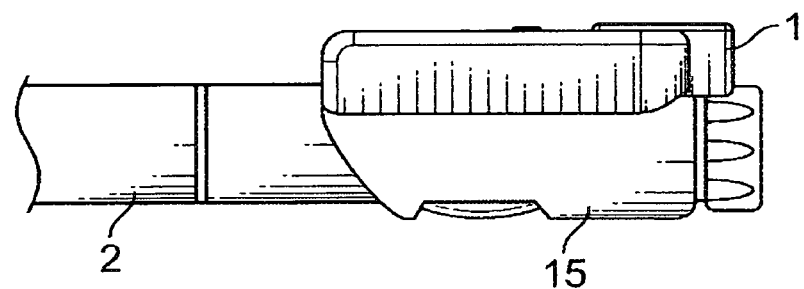
FIG. 10 is a side elevation of the monitoring device on the injection pen.
Figure 11:
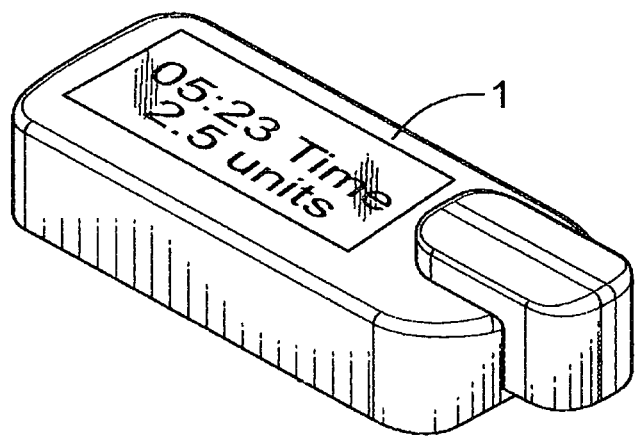
FIG. 11 is an enlarged perspective view from above and one side of the monitoring device.
Figure 12:
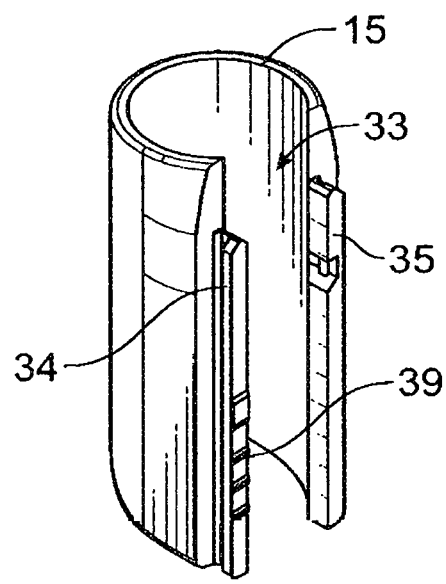
FIG. 12 is an enlarged perspective view from above and one side of the sleeve of FIG. 8 having pen identifiers thereon in the form of bump-like projections for communicating the identity of the injection pen to the monitoring device.
Figure 13:
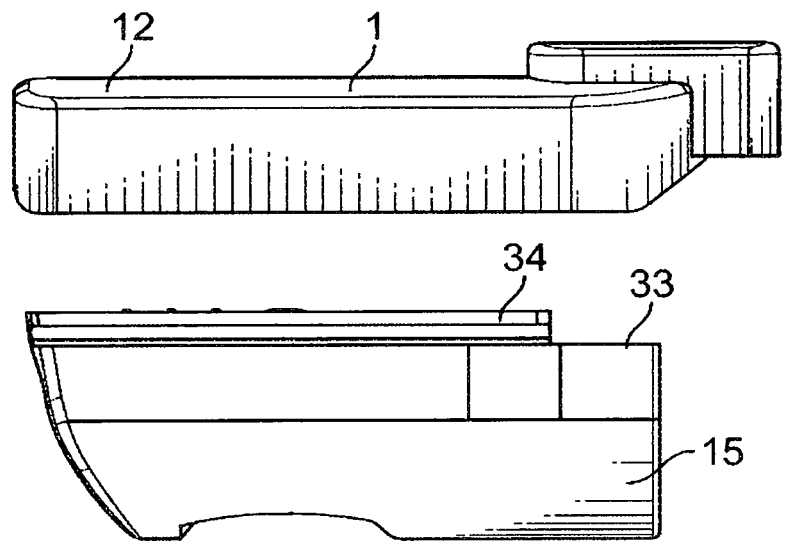
FIG. 13 is a further enlarged side elevation of the monitoring device disposed over the sleeve.
Figure 14:
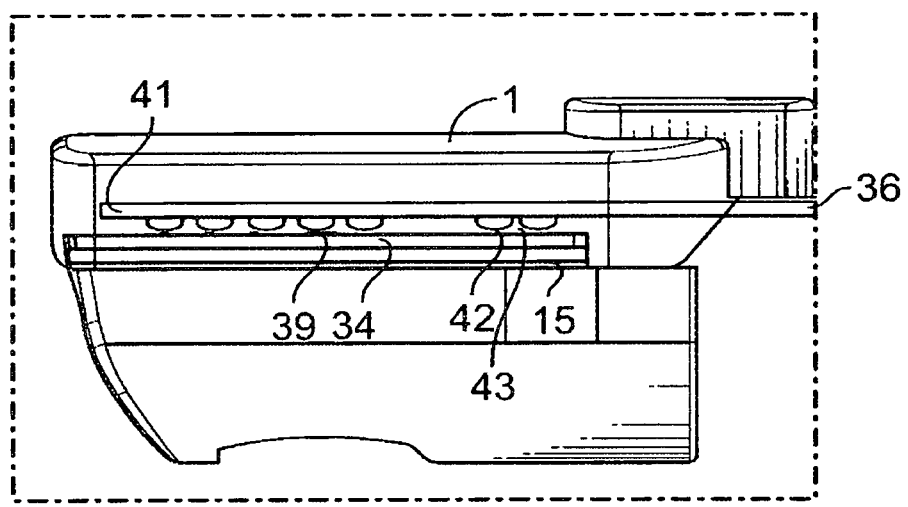
FIG. 14 is a further enlarged side elevation of the monitoring device showing the identifier sensors in the form of pressure switches for recognising the bump-like projections on the sleeve.

The monitoring device 1 is made up of a housing 1a containing a motion detection system 8 for detecting rotational and translational or longitudinal movement of the shaft on which the dose selector 5 and the push button 6 are located. The motion detection system 8 is an optical motion detection system 8 and is made up of an optical sensor 9 for sensing movement of the dose selector 5/push button 6 shaft, in communication with a display 10, a communications module 11 for transmitting data from the monitoring device (in the present embodiment via a Bluetooth (Trade Mark) unit 12) and a central processing unit (CPU) 13 together with a memory 14. FIG. 6 shows a functional block diagram of the motion detection system 8.

Where the monitoring device 1 is to be retrofitted to a conventional "non-smart" insulin pen 2, the monitoring device 1 can be secured to the insulin pen 2 via an intermediate mounting device such as an annular sleeve 15 adapted to be mounted securely on the insulin pen 2 whilst also removably supporting the monitoring device 1 in place. The sleeve 15 is shaped and sized to locate the monitoring device adjacent the dose selector 5 so that the optical sensor 9 can detect movement of the dose selector 5/push button 6 shaft.

The intermediate mounting device or annular sleeve 15 can be shaped, contoured and sized to be injection pen specific i.e. match the diameter, shape and design of individual injection pens manufactured by various manufacturers so that the monitoring device 1 of the invention is automatically correctly located and positioned on the injection pen. As shall be explained more fully below, the annular sleeve 15 can also be provided with physical or software-related identification codes unique to individual injection pens which are communicable with and recognisable by the monitoring device 1 so that monitoring device 1 can automatically recognize individual injection pens.

As indicated above, the monitoring device 1 described above can be incorporated into an insulin pen 2 during manufacture or retrofitted to existing insulin pens 2 to create smart insulin pens 2. As described in FIG. 7, in use, where movement of the push button 6/plunger shaft is detected 17 by the monitoring device, the dose display 7 is reset 18 to indicate motion (the plunger/push button 6 normal resting position being in the down disposition). The dose display 7 continually displays the dose corresponding with the plunger position dialled by the user 19 via the dose selector 5.

The monitoring device 1 monitors 20 the Peak Value (the largest reading/movement i.e. dose measured by the optical sensor 9 which it is assumed the user will inject) to determine the start of injection while the display 1O also displays additional warning/information messages 21 based on previous usage data stored in the memory 1.

Completion of injection is detected 22 by measuring return travel of the shaft back to a fully down state.

If the injection is complete 23, the display 10 is updated 24 to confirm acknowledgement of completion together with the time of the injection and the dosage. If the injection is not complete 23 within a pre-determined time 25, an error is communicated to the user via an audible or visual signal.

All success/error data is logged 26 to the RAM memory 14 together with other optional environmental information such as temperature or other sensor data where appropriate sensors are present in the monitoring device 1.

Where the monitoring device 1 is in communication with another smart device such as a smartphone 27 via an app, data is transmitted/received 28 between the monitoring device 1 and the smartphone. Actions required to be displayed are then queried 29 and where display notifications are received from the smartphone app, they are displayed 30.

Following display of the notifications or where no notification is to be displayed, the display 10 is updated 31 to show the time elapsed since the last injection for the user.

The monitoring device 1 then returns to an idle state 32 to await the next injection and/or a message/notification from the app.

FIGS. 8 to 21 show is a second embodiment of a monitoring device 1 of the invention broadly similar in form and function to the monitoring device of FIGS. 1 to 8 but being provided with various sensors such as a mounting sensor, an accelerometer sensor and a temperature sensor to provide the monitoring device 1 with additional functionalities. Like numerals indicate like parts.

As shown in the drawings, the monitoring device 1 is mountable on a conventional insulin pen 2 via an annular sleeve 15 peculiar to the insulin pen 2. The annular sleeve 15 is open to define an elongate slit 33 in the sleeve 15. At the slit 33, the annular sleeve 15 is provided with first and second opposite elongate rails 34, 35 respectively for engagement with complimentary rails 36, 37 on the monitoring device 1 for securing the monitoring device 1 to the sleeve 15. The first rail of the sleeve 15 is provided with a series of pen identifiers 38 in the form of bump-like projections 39 for communicating the identity of the injection pen 2 to the monitoring device 1.

Similarly, the monitoring device 1 is provided with a series of pressure sensor switches 40 on its corresponding rail 36 so that upon attachment of the monitoring device 1 to the pen specific sleeve 15 on an injection pen 2, the pressure switches 40 are activated by the bump-like projections 39. The monitoring device 1 is preprogrammed to identify the injection pen in accordance with the number, sequence or spacing of pressure switches 40 activated via a printed circuit board (PCB) 41 in communication with the pressure sensor switches 40 i.e. the series of pressure switches 40 encodes the sleeve 15 type which is in turn unique to the type of injection pen 2.

In the present embodiment, the sleeve 15 is further provided with a mounting position identifier 42 also on the elongate rail 34 in the form of a rib 43. As with the bump-like projections 39, the rib 43 activates corresponding mounting pressure sensor switches 44 on the elongate rail 36 of the monitoring device 15 to signify to the user that the monitoring device 1 is correctly mounted and positioned on the injection pen 2.

As shown particularly in FIGS. 15 to 17, the monitoring device 1 of the present embodiment, in addition to the optical sensor 9 and the pressure sensor switches 40, 42, the monitoring device 1 is also provided with a temperature sensor 45 for monitoring the temperature of the injection pen 2. The temperature sensor 45 is in communication with the CPU 13 so that the user can be advised when the injection pen 2 is being stored at a temperature outside the normally recommended temperature range for the medicament in the injection pen 2. For example, for insulin drugs, the efficacy of the drug can be compromised outside a temperature range of 5 to 28° C.

The monitoring device is further provided with an accelerometer sensor chip 46 for detecting movement of the plunger shaft 6. More particularly, the accelerometer 46 sensor is adapted to detect vibrations of the plunger shaft in X, Y and Z planes to determine whether or not a dose is in fact delivered by the injection pen 2. As will be appreciated by those skilled in the art, although the optical sensor 9 can detect adjustment/rotation of the dose selector 7 and plunger shaft 6 prior to injection, the optical sensor 9 is unable to determine whether the programmed dose is in fact delivered by the user. However, as the accelerometer 46 can detect vibrations, the accelerometer can be calibrated and programmed to distinguish between rotation/dose adjustment and actual injection in accordance with vibration patterns. Accordingly, the accelerometer 46 serves an injection confirmation sensor to confirm that the dosage detected by the optical sensor 9 has in fact been injected by the user.

The accelerometer 46 performs the necessary analysis of vibrations in accordance with the unique vibration patterns of the specific injection pen 2 as detected by the monitoring device via the sleeve 15 as described above. The accelerometer 46 is in communication with the CPU 13.

The monitoring device 1 of the present embodiment is further provided with a communications module 11 (e.g. Bluetooth, USB etc.) as previously described together with a power source in the form of a battery 4 7.

Figure 18:
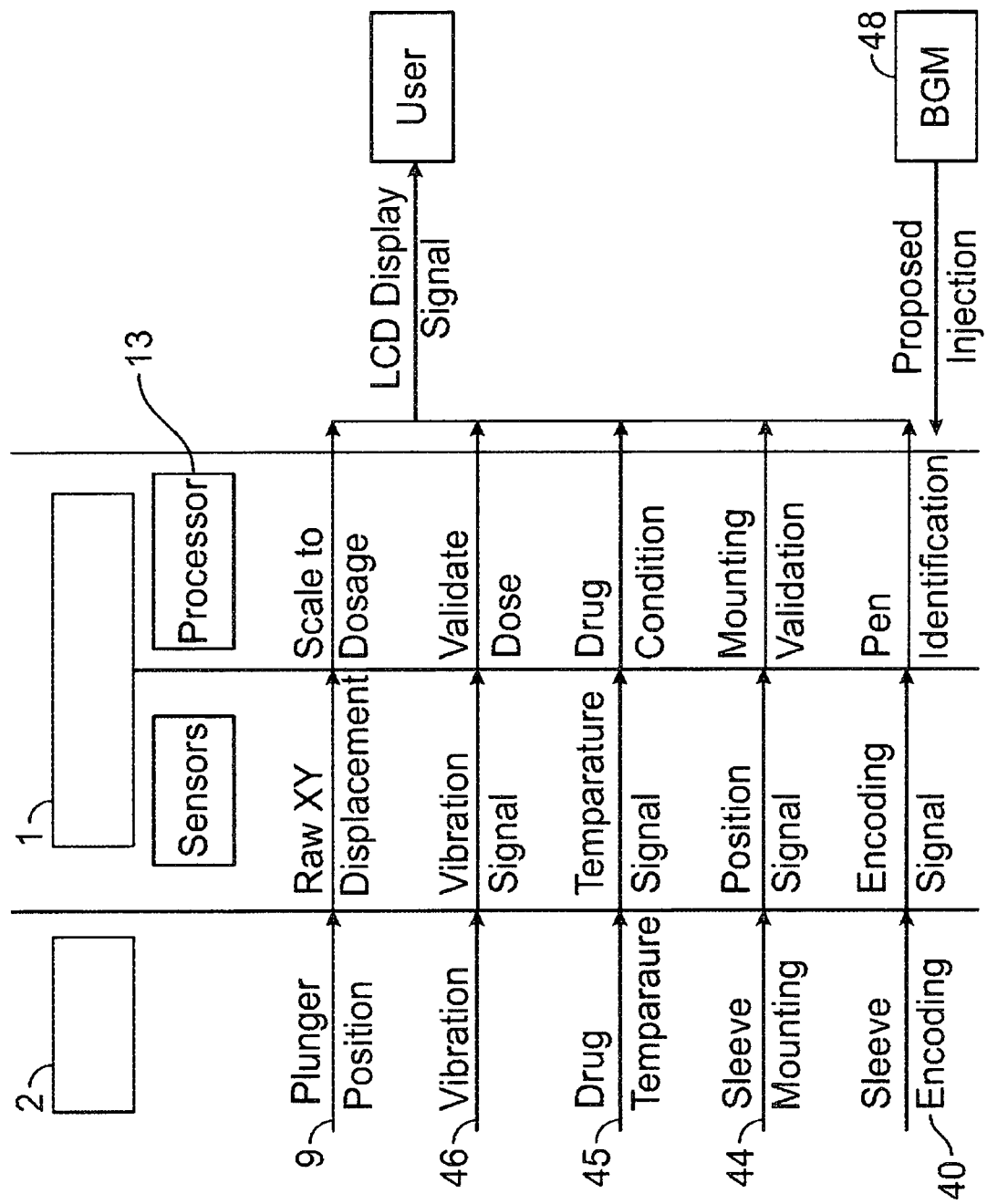
FIG. 18 is a schematic representation of the interface between the injection pen, the monitoring device and the sensors and processor within the monitoring device and communication of the relevant data to the user.

FIG. 18 shows a schematic representation summarizing the interface between the injection pen 2 and the sensors of the monitoring device 1 namely the optical sensor 9, the injection pen identifier pressure sensors 40, the mounting position pressure sensors 44, the temperature sensor 45 and the accelerometer 46 in communication with the processor 13. As shown in the drawing, in response to a determination by a Blood Glucose Monitor 48, a user elects to perform an injection as previously described. Previously, the pressure switches 40 of the monitoring device 1 has identified the injection pen 2 on which it is mounted via the bump-like projections 39 on sleeve 2 and whether the monitoring device 1 is correctly mounted and positioned on the injection pen via the mounting pressure switches 44. The temperature of the medicament is also monitored by the temperature sensor 45 while dosage selection and adjustment is detected by the optical sensor 9. Finally, once the user injects the selected dosage, confirmation of injection is detected by the accelerometer 46.

Figure 19:
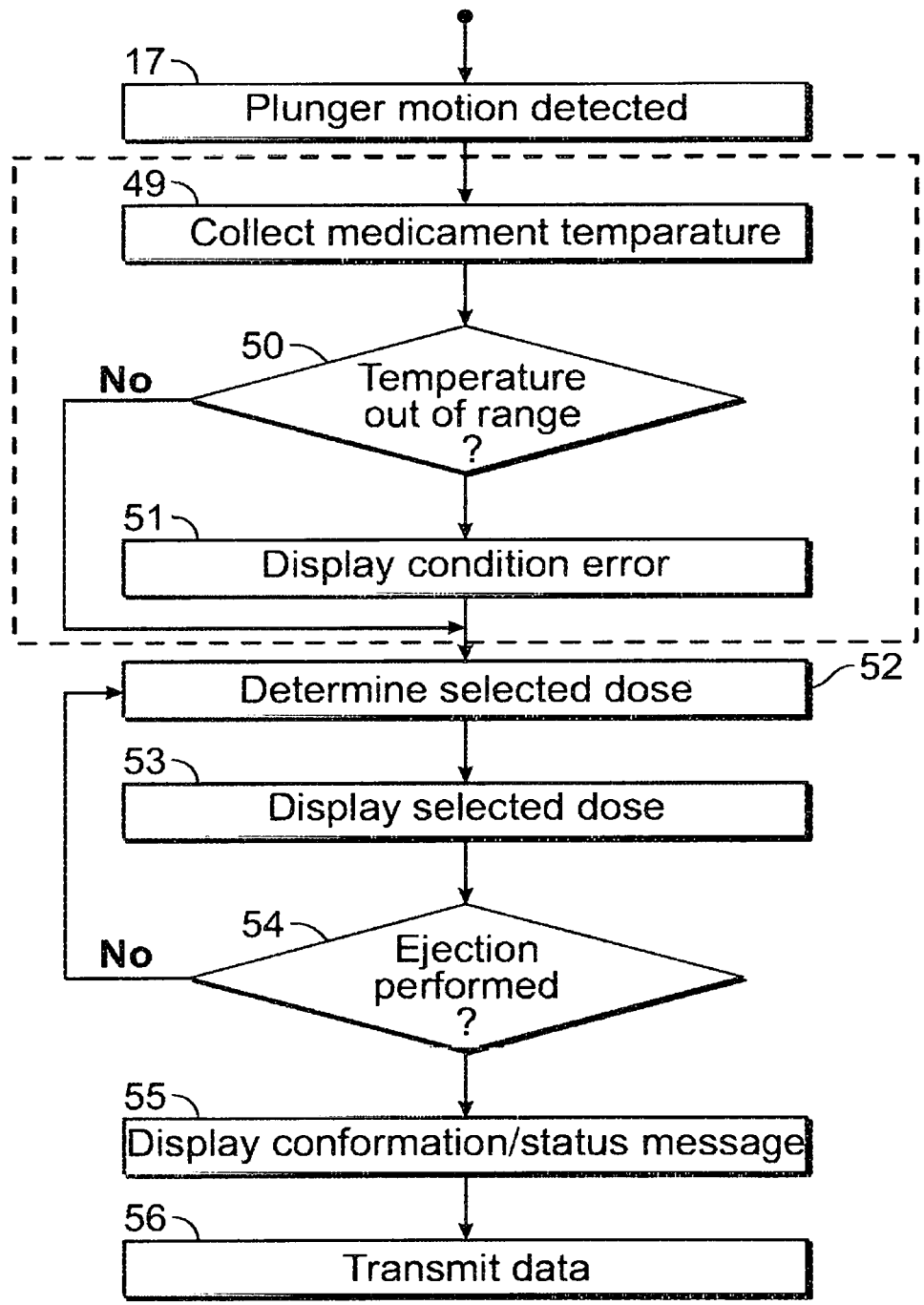
FIG. 19 is a general flow diagram of the operation of the monitoring device of the second embodiment of the invention.
Figure 20:
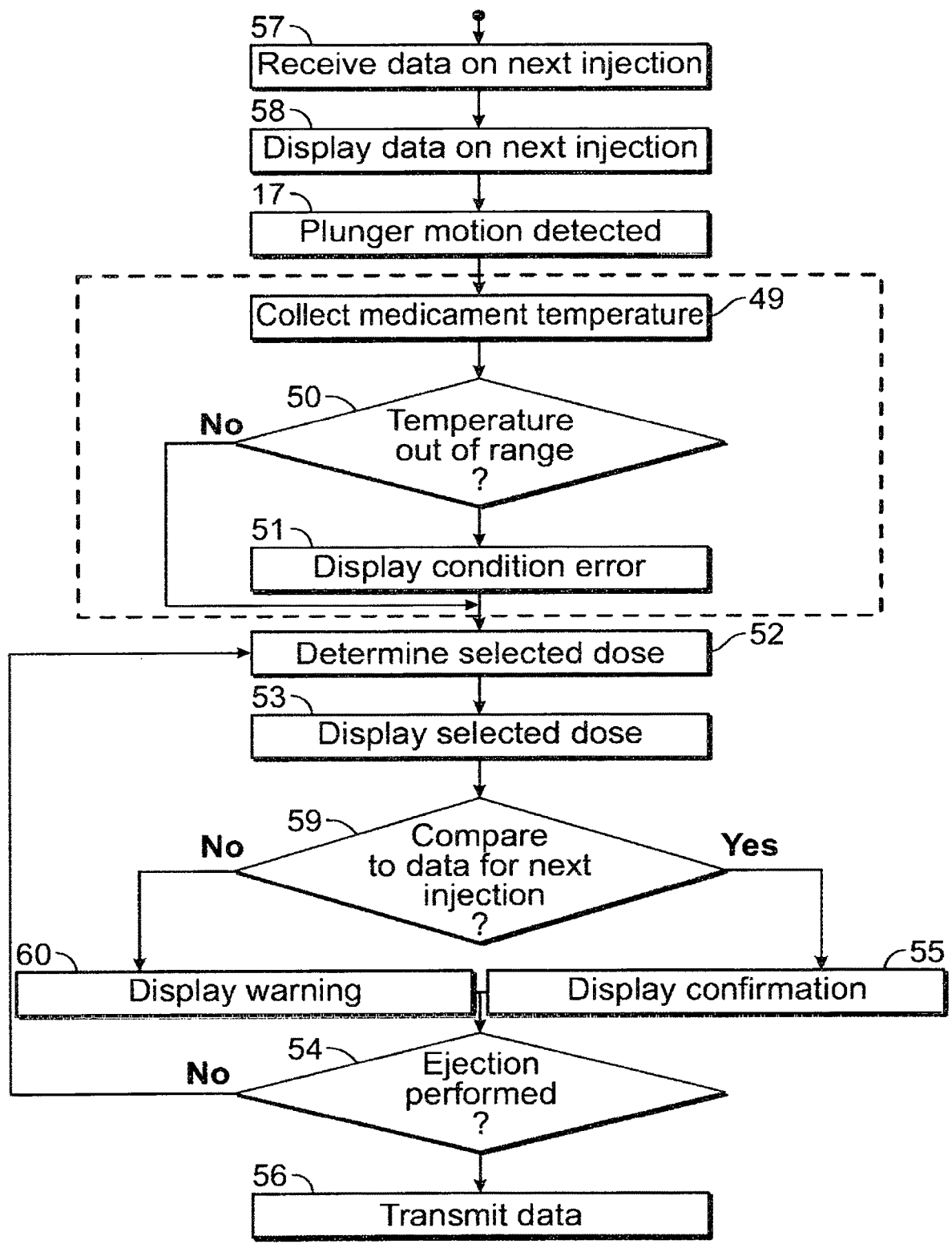
FIG. 20 is a more detailed flow diagram of the operation of the monitoring device showing the incorrect dosage warning.
Figure 21:
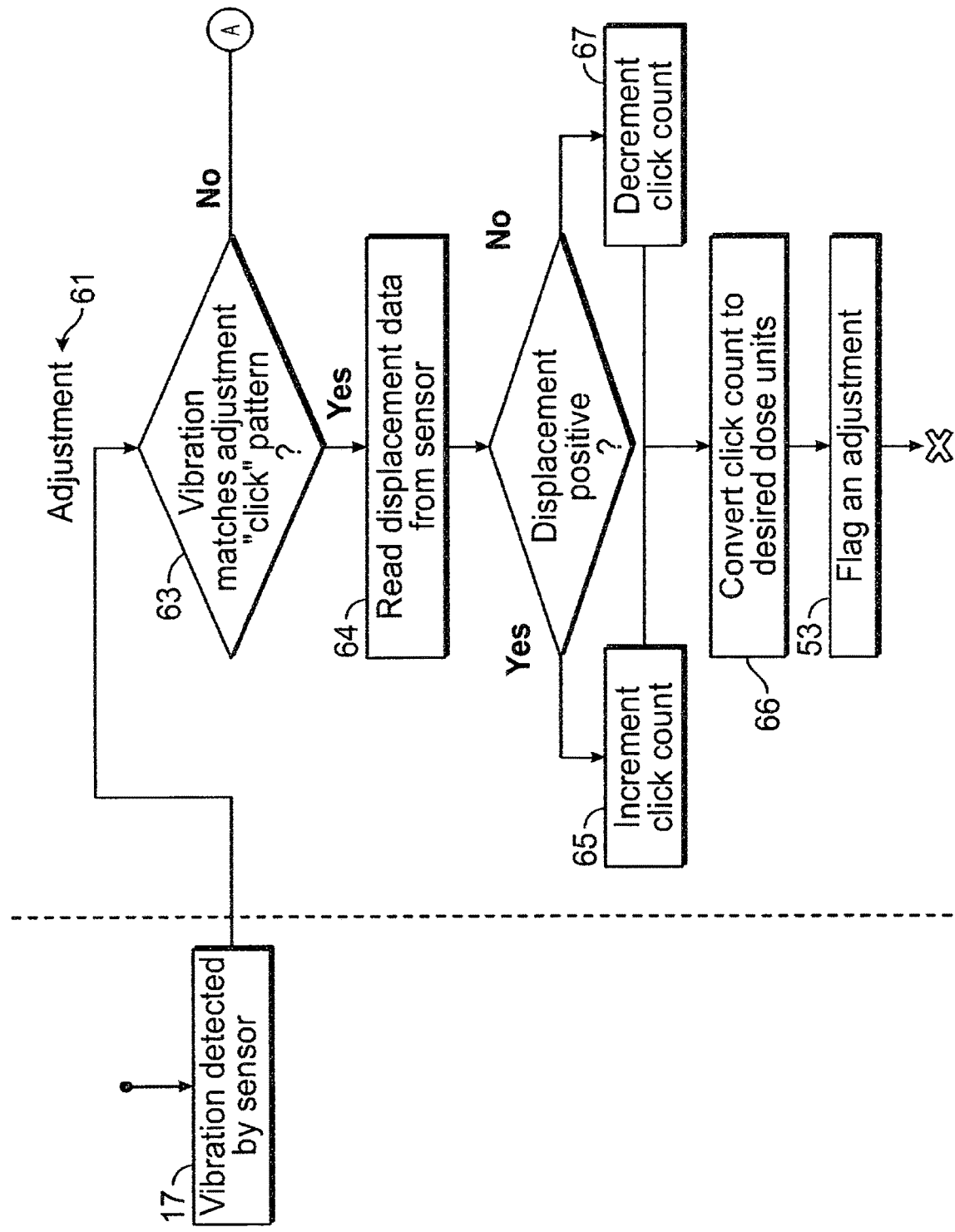
FIG. 21 is flow diagram of the method of operation and detection of the accelerometer sensor.

FIGS. 19 to 21 are flow diagrams showing use and operation of the monitoring device 1 of the present embodiment of the invention. The steps in the operation and use of monitoring device are broadly similar to those described in FIG. 7 for the use of the first embodiment of the monitoring device 1.

As shown in FIG. 17, upon plunger motion detection 17 by the optical sensor 9, medicament temperature is detected 49 by the temperature sensor 45. If the temperature is outside the correct range an error message is displayed 51. The dose selected by the user as detected by the optical sensor 9 is determined 52 and displayed 53 while the accelerometer sensor 46 determines whether an injection is actually performed 54. Confirmation of the injection and injection pen status is then displayed 55 and the data transmitted 56 to a smart device via communications module 11.

As shown in FIG. 20, the monitoring device 1 of the invention can also receive instructions/data from the external smart device or computer e.g. data on the next injection to be performed 57 which is displayed 58 on the device for the user. Following manual dose selection 52, 53 by the user, the monitoring device 1 then compares 59 the selected dose with the instruction received for the next injection and transmits a warning 60 to the user where the incorrect dose has been selected.

As shown in FIG. 21, the accelerometer sensor 46 is adapted to distinguish between adjustment 61 of the dose selector 5 and injection 62. As indicated above, the accelerometer sensor 46 can be programmed to recognise and distinguish vibrations unique to such operations in all injection pens. Where a vibration detected by the accelerometer sensor 46 matches an adjustment click pattern 63, the displacement determined by the optical sensor 9 is read 64. Where the displacement is positive a click count is incremented 65 and converted to dose units 66 and the adjustment is displayed 53 as previously described. However, where the displacement is not positive, the click count is decremented 67 and converted to dose units 66 as before.

Where the vibration pattern does not match an adjustment click pattern but matches an injection vibration pattern 68, the displacement data is read as before 64, the final dose position is calculated 69, the click count is decremented 67 and converted to dose units 66. If the final dose is zero 70, a complete injection is flagged 71 and a warning is issued 72 if only a partial injection was performed.

If the vibration detected by accelerometer 46 was identified as neither an adjustment vibration nor an injection vibration, the vibration can be ignored.

Figure 22:
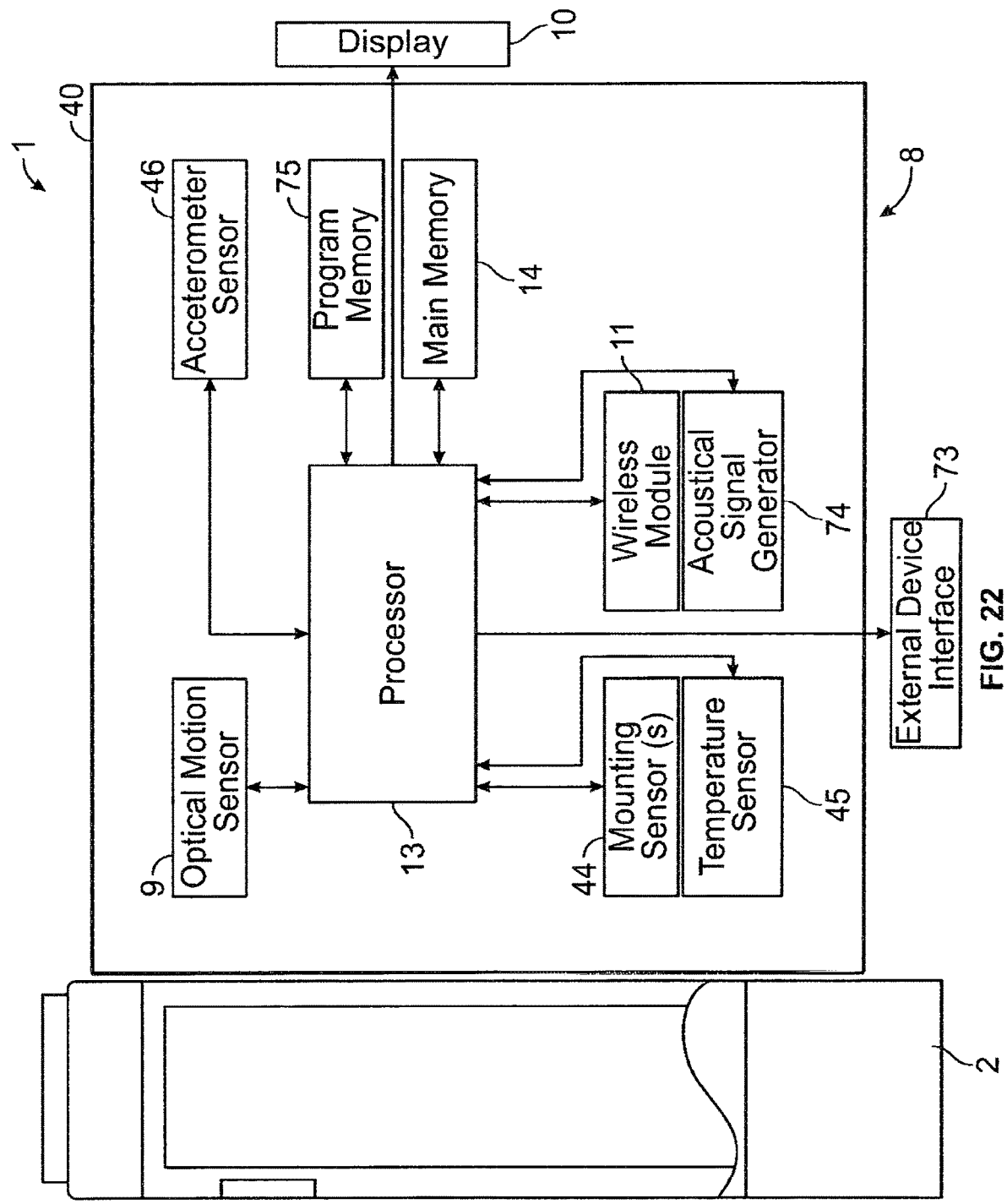
FIG. 22 is a functional block diagram of the motion detection system of the second embodiment of the monitoring device.

FIG. 22 is a functional block diagram of the motion detection system 8 of the second embodiment of the monitoring device 1 broadly similar to diagram of FIG. 6 but showing the additional functionalities of the second embodiment. Generally, the motion detection system 8 is made up of the optical sensor 9 and the accelerometer sensor 46 for sensing movement of the dose selector 5/push button 6 shaft, in communication with a display 10, a wireless communications module 11 for transmitting data from the monitoring device 1 and a processor 13 together with a main memory 14. As described above, the monitoring device 1 of the present embodiment is additionally provided with pen identifier pressure and mounting sensors 40, 44 so that the monitoring device 1 can firstly identify the injection pen 2 on which it is mounted and, secondly, ensure that the monitoring device 1 is correctly mounted on the injection pen 2.

A temperature sensor 45 is also provided to ensure that the medicament within the injection pen 2 is maintained at the correct temperature.

As shown in the drawing, the optical motion sensor 9, the accelerometer sensor 46, the pen identifier pressure sensors 40, the mounting sensors 44 and the temperature sensor 45 are in communication with the processor 13 which is in turn communicable with an external device interface 73 while the wireless module 11 can communicate with external smart devices such as mobile phones and the like.

As shown in the drawing, the monitoring device 1 can be additionally provided with an acoustical signal generator 7 4 to issue audible alarms to a user in addition to the visible display 10.

A program memory 75 is also provided in the monitoring device 1.

In summary, the present invention provides a smart injection pen such as an insulin pen or a monitoring device that can be retrofitted to an existing pen in a clip-on relationship to assist in maintaining optimum medical control e.g. diabetic control. The clip-on device can be adapted to fit a specific brand or range of insulin pens to hold and align the apparatus in optical contact with the pen. A suitable clip-on arrangement is described in PCT Patent Specification No. WO 2010/128493.

The devices of the invention contain an optical sensor such as that used in modern optical computer mice e.g. an ADNS-7530 Integrated molded lead-frame DIP Sensor. Other suitable optical sensors are the ADNS 2080 and ADNS 3000 all available from Pixart (Trade Mark). When the device is mounted firmly and precisely onto an insulin pen or incorporated into an insulin pen such that the optical sensor is positioned over the base of the dosage knob, the sensor can record the rotational motion traveled by the knob as well as its longitudinal movement or extension out of the body of the pen where such information is available. If desired, the monitoring device 1 of the invention can employ two or more optical sensors as required.

The optical sensor can be any suitable optical sensor and any motion detecting wavelength can be used e.g. infra-red, visible, UV, laser LED and visible LED etc.

The motion detection systems employed in the monitoring device of the invention can detect translational movement (the optical sensor) and vibrational movement (the accelerometer) that corresponds to the rotational and linear travel of the plunger of the pen. This data can be directly correlated with the dose that a user has selected through a simple scaling factor processed via an onboard CPU. Either the raw or calibrated data can be stored internally on the device together with an accurate time stamp for later retrieval.

The device is adapted to download this data via wired or wireless communications ports e.g. via a Bluetooth interface to download data to a personal computer or a smartphone or similar device. The communications port can also be used to configure or calibrate the device remotely if needed.

Suitable Bluetooth modules include the Texas Instruments (Trade Mark) CC2540 2.4 GHz Bluetooth Low Energy System-on-Chip Solution while suitable microcontrollers include Texas Instruments (Trade Mark) MSP430F67791 Mixed Signal Microcontroller.

The monitoring device 1 of the invention has relatively few components and is made up of inexpensive components and is cost-efficient to manufacture.

The invention claimed is:

1. A monitoring device for monitoring the injection of a medicine using an injection device, the monitoring device comprising:
   a sleeve configured to be removably mounted to an injection device, where the sleeve comprises:
      an annular shape having an elongate slit used to removably mount the sleeve to the injection device; and
      an elongate rail having a pen identifier,
   a housing comprising:
      an optical motion detection system that passively detects both rotational and longitudinal continuous movement of a shaft of the injection device relative to a body housing of the injection device using an optical sensor as the shaft moves distally and axially outward from the body housing during dose setting and as the shaft moves proximally and axially back into the body housing during dose delivery when the housing and sleeve is attached to an outside surface of the body housing of the injection device, where the housing is rotationally and axially fixed relative to the body housing such that all components of motion detection system are contained within the housing and do not move relative to the body housing, where the optical sensor is positioned such that it projects over the shaft to track both the axial and rotational movement of the shaft in a proximal direction during injection of a set dose of medicine and in a distal direction during dose setting; and
      a complimentary rail configured to removably engage with the elongate rail such that when engaged, the housing and the sleeve are securely attached and the pen identifier is in operative communication with the optical motion detection system,
   wherein the detection of the shaft movement does not involve mechanical movement of any part of the motion detection system.

2. The monitoring device as claimed in claim 1 wherein the optical sensor is selected from the group comprising a visible light, infra red, laser, ultra violet, and LED optical sensors.

3. The monitoring device as claimed in claim 1 wherein the optical motion detection system comprises a memory, a CPU and a display communicable with the optical sensor.

4. The monitoring device as claimed in claim 3 wherein the optical motion detection system comprises a communications module for communicating between the monitoring device and an external smart device.

5. The monitoring device as claimed in claim 4 wherein the communications module comprises a Bluetooth communications module.

6. The monitoring device as claimed in claim 4 wherein the external smart device is selected from the group comprising a smartphone, computer or handheld device.

7. The monitoring device as claimed in claim 1 wherein the device further comprises an accelerometer sensor that detects movement of the shaft during dose delivery through sensing vibration of the injection device such that the monitoring device distinguishes dose setting or dose adjustment from actual dose injection.

8. The monitoring device as claimed in claim 1 wherein the device further comprises a temperature sensor for monitoring the temperature of the medicine.

9. The monitoring device as claimed in claim 1 wherein the monitoring device comprises an attachment means for retrofitting the monitoring device to an injection device to create a smart injection device.

10. The monitoring device as claimed in claim 9 wherein the attachment means comprises a detachable attachment means.

11. The monitoring device as claimed in claim 1 wherein the sleeve is unique to the injection device.

12. The monitoring device as claimed in claim 11 wherein the injection device identifier comprises a projection on the sleeve.

13. The monitoring device as claimed in claim 12 wherein the monitoring device comprises an injection device identifier sensor.

14. The monitoring device as claimed in claim 13 wherein the injection device identifier sensor comprises a pressure sensor.

15. The monitoring device as claimed in claim 1 wherein the injection device comprises an injection pen.

16. An injection pen comprising a device as claimed in claim 1.

17. The injection pen as claimed in claim 16 wherein the injection pen is an insulin injection pen.

18. The monitoring device as claimed in claim 1 further comprises a plurality pressure sensor switches that engage projections on the sleeve when the monitoring device housing is attached to the sleeve.

19. A monitoring device for removable attachment to a pen type injection device, where the monitoring device comprises:
  a housing comprising an optical motion detection system that passively detects both rotational and directional movement of a part of an injection device using an optical sensor when the housing is attached to an outside surface of a body housing of the injection device, where the housing is rotationally and axially fixed relative to the body housing such that all components of motion detection system are contained within the housing and do not move relative to the body housing, where the optical sensor is positioned such that it projects over the moving part of the injection device to track both the axial and rotational movement of the part in a proximal direction during injection of a set dose and the axial movement of part of the injection device in a distal direction relative to the body housing during dose setting; and
  a removable mounting device that releasably attaches to the body housing of the injection device and to the monitoring device housing, where the monitoring device housing further comprises a plurality sensor switches that engage projections on the mounting device when the monitoring device housing is attached to the mounting device,
  wherein the engagement of the sensor switches with the projections allows the pen type injection device to be identified.

* * * * *